United States Patent [19]

Matsutani et al.

[11] Patent Number: 5,816,807
[45] Date of Patent: Oct. 6, 1998

[54] ROTARY DRILLING INSTRUMENT

[75] Inventors: Kanji Matsutani; Satoshi Tezuka; Kaoru Ohgane, all of Tochigi-ken, Japan

[73] Assignee: Kabushiki Kaisha Matsutani Seisakusho, Tochigi-ken, Japan

[21] Appl. No.: 594,558

[22] Filed: Jan. 31, 1996

[30] Foreign Application Priority Data

Feb. 2, 1995 [JP] Japan ..................... 7-015802

[51] Int. Cl.$^6$ ........................... A61C 3/02
[52] U.S. Cl. ............................... 433/165
[58] Field of Search ................... 433/102, 105, 433/166; 408/144

[56] References Cited

U.S. PATENT DOCUMENTS 4,315,742  2/1982  Nash et al. ............... 433/86
5,259,398  11/1993  Vrespa .................... 128/898
5,297,909  3/1994  Tsay et al. ............... 411/29

*Primary Examiner*—Nicholas D. Lucchesi
*Attorney, Agent, or Firm*—Townsend&Banta

[57] ABSTRACT

There is provided a rotary drilling instrument having uniform hardness, free from rust, and made of austenitic stainless steel possessing a hardness substantially the same as quenched steel or quenched martensitic stainless steel. The rotary drilling instrument is formed with a cutting section formed at one end of a body, a shank formed at the other end of the body, and a neck portion formed between the cutting section and the shank. The rotary drilling instrument is made of austenitic stainless steel having a fibriform organization elongated in a longitudinal direction and has a surface having a predetermined hardness.

5 Claims, 2 Drawing Sheets

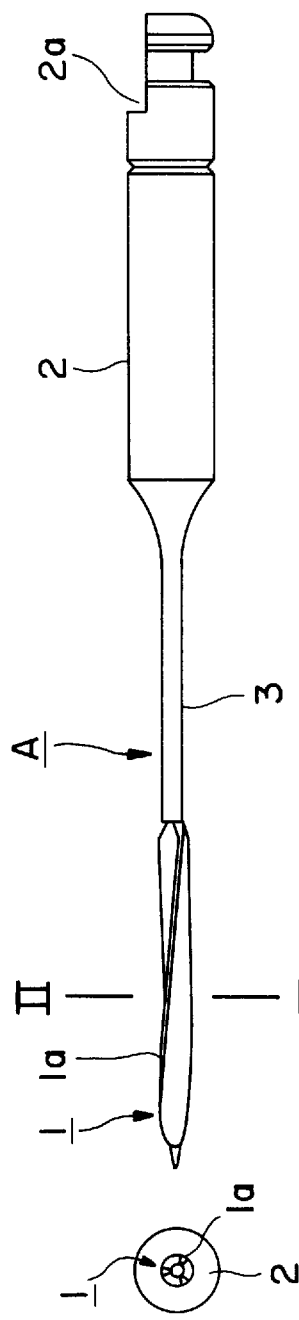
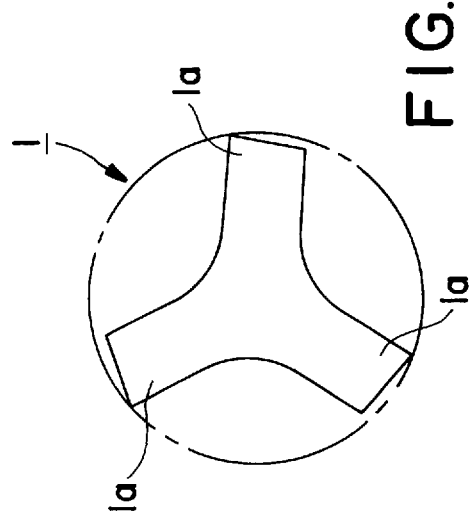
FIG. 1C
FIG. 1A
FIG. 2
FIG. 1B

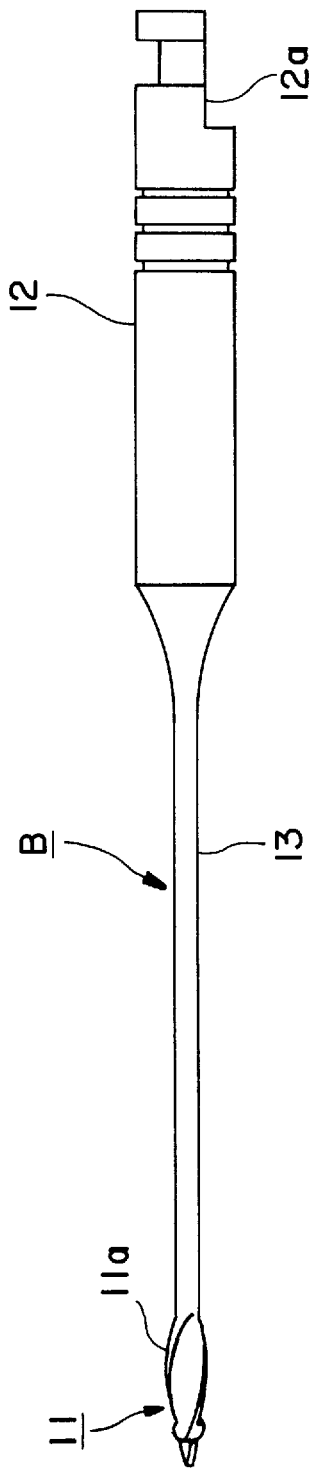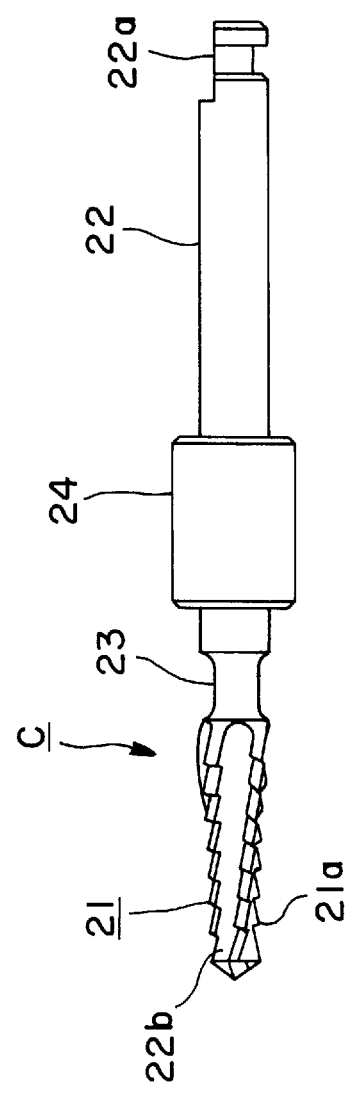

ROTARY DRILLING INSTRUMENT

BACKGROUND OF THE INVENTION

1. Field of the Invention

This invention relates to a rotary drilling instrument for dentistry and, more particularly, to a Peeso reamer, a Gates drill (a Gates-Glidden drill), and a drill for implantation made of austenitic stainless steel.

2. Description of Prior Art

In dental treatments, a relatively hard layer such as a tooth surface or dentin formed at a root canal may be opened or drilled, and instruments such as the Peeso reamer and the Gates drill have served in order to drill such a layer. While implantation treatments, in which after a post is implanted in patient's jaw and an artificial tooth is attached on the post, are conducted in several ways, rotary drilling instruments or drills for implantation are used even for drilling the jaw. Those rotary drilling instruments for dentistry can acquire their hardness and be capable of drilling the dentin and bone by thermal application after machined into desired shapes. Those rotary drilling instruments are made from materials that become hardened upon quench, such as carbon tool steel and martensitic stainless steel. Such rotary drilling instruments are subject to sterilization in which those instruments are exposed to a high temperature and steam atmosphere in, for example, an autoclave at every treatment, and tend to be used in this way repetitively during their life.

Since conventional rotary drilling instruments are made of steel or martensitic stainless steel as described above, there raises a problem that the instruments may rust unless made subject to a sufficient rust preventive treatment after sterilization. For example, most endodontic instruments such as reamers, files, cleansers, and broaches are made of austenitic stainless steel which never rusts. However, no one thought that the Peeso reamer, the Gates drill, and the drill for implantation were to be made of the austenitic stainless steel that does not possess hardenability, because such instruments need hardness of a certain degree to function to sufficiently drill the dentin and bone. Where the medical instruments must be free from rust, it is currently required to develop a Peeso reamer or a Gates drill free from rust.

It is generally difficult to heat the entire material uniformly when hardened, so that a rotary drilling instrument made of the martensitic stainless steel or tool steel is prone to have local deviations from uniform hardness. These instruments therefore raise a problem that the instruments may not have sufficient hardness to drill the dentin. In particular, where drilling a root canal, an instrument is required to have uniform hardness as a whole, and in case that the instrument comes to be broken, the instrument needs to be broken at a prescribed point except their blades. Accordingly, such deviations of hardness raise a fatal problem.

Those rotary drilling instruments are attached to a rotary driving tool called as a hand piece, which is handled by a dentist to conduct a dental therapy. It is generally understood that the Peeso reamer and the Gates drill cannot always maintain their rotary axis to be straight and the rotary axis tends to curve, so that a bending stress may be repetitively exerted on the instrument. When the instruments have deviations of hardness, the instruments lack uniformity of their life, thereby impairing reliability on their quality.

SUMMARY OF THE INVENTION

It is an object of the invention to provide a rotary drilling instrument having a uniform hardness, being free from rust, and being made of austenitic stainless steel possessing a hardness substantially the same as a quenched steel or quenched martensitic stainless steel.

To solve the problem above, a rotary drilling instrument according to the present invention is formed with a cutting section formed at one end of a body, a shank formed at the other end of the body, and a neck portion formed between the cutting section and the shank. The rotary drilling instrument is made of austenitic stainless steel having a fibriform organization elongated in a longitudinal direction, and has a surface thereof having a predetermined hardness.

The rotary drilling instrument never rusts even if subject to repetitive use and repetitive sterilization in an autoclave and can maintain a clean condition at any time, because the instrument is made of austenitic stainless steel. A metal organization of the instrument mechanically elongated in the longitudinal direction to become fibriform by means of cold drawing of the austenitic stainless steel, can effectuate a stable uniform hardness and stably harden the surface thereof to a prescribed hardness (for example, Hv 500 or more) as well as stably improve the hardness. Accordingly, no part will be chipped during dental treatments.

Since the fibriform metal organization possesses a strong hardness against bending as different from a grainy organization the martensitic stainless steel, the rotary drilling instrument can serve well for a treatment with the smoothly bent neck portion when molars are treated, even though the hand piece cannot be faced to the affected area precisely.

BRIEF DESCRIPTION OF THE DRAWINGS

The above and other objects and features of the invention are apparent to those skilled in the art from the following preferred embodiments thereof when considered in conjunction with the accompanied drawings, in which:

FIG. 1 is an illustration showing a construction of a Peeso reamer according to the invention;

FIG. 2 is a cross section, taken along II—II line in FIG. 1, showing the reamer;

FIG. 3 is an illustration showing a construction of a Gates drill according to the invention; and FIG. 4 is an illustration showing a drill for implantation according to the invention.

DETAILED DESCRIPTION OF THE PREFERRED EMBODIMENTS

Referring to FIGS. 1, 2, a Peeso reamer, serving as a rotary drilling instrument, of a first embodiment according to the invention is described. FIG. 1 is a side view showing constitution of the Peeso reamer; FIG. 2 is a cross section taken along II—II line in FIG. 1. The Peeso reamer is an intracanal instrument for dental treatment and is used for drilling dentin of teeth by fixing one end of the reamer to a hand piece to rotate the reamer.

In FIG. 1, the Peeso reamer A is formed with a cutting section 1 located between the tip and a midpoint of a reamer body having a predetermined length and formed with a shank 2 having a predetermined length located at the other end of the reamer body. A neck portion 3 is formed between the cutting section 1 and the shank 2. Three blades 1a are provided at the cutting section 1; each blade 1a is arranged at a prescribed twisted angle; a side contour of the blade 1a is made straight. The Peeso reamer A is attached to a chuck of a rotary driving apparatus such as a hand piece not shown and is controlled to rotate. The shank 2 therefore extends straight and is formed with an orientation portion 2a corresponding to the chuck. The neck portion 3 extends straight with a diameter smaller than any of the outer diameter of the cutting section 1 and the outer diameter of the shank 2. The neck portion 3 has rounded connections of a predetermined curvature connected to the cutting section 1 and the shank 2. The neck portion 3 is first broken down by torsional stress and bending stress exerted thereto as if functioning as a fuse in case when drilling operation is disturbed during the treatment.

The reamer body of the Peeso reamer thus formed is made of an austenitic stainless steel. The austenitic stainless steel possesses a rust free nature, but cannot be hardened by quenching, and is hardened only by cold drawing. The austenitic stainless steel is hardened by cold drawing with a predetermined reduction rate to form a structure with a diameter substantially the same as the diameter (about 2.3 millimeters) of the shank 2 of the Peeso reamer, and upon a proper adjustment of the reduction rate the austenitic stainless steel can be modified to have a desired hardness, for example, Hv 500 or more.

When the austenitic stainless steel is subject to the cold drawing to render the organization thereof elongated in the axial direction of the drawn material and to become fibriform, the austenitic stainless steel can improve the bending strength thereof and effectuate uniform strength of the entire drawn material without deviation. After the drawn material is cut to a length corresponding to the targeted Peeso reamer A, the cut material is machined to form the Peeso reamer A.

The material obtained by cold drawn from the austenitic stainless steel has a coaxial hardness profile. That is, the surface of the material becomes the hardest while the material is softer closer to the center of the material. To form an intermediate material for the Peeso reamer A, the hardest surface layer is removed by machining. Since the furnished surface is expected to be superficially hardened by virtue of the vanishing effect, the surface hardness of the reamer body of the Peeso reamer A can be maintained at the value above upon setting the surface hardness of the drawn material at Hv 500 or more.

The cutting section 1 and the neck portion 3 are formed by grinding the intermediate material in a cylindrical shape in which the austenitic stainless steel thus has been machined. Specifically, the cutting section 1 is formed with spiral blades 1a by grinding the material and pushing a hone in spiral contact with the surface of the material. The neck portion 3 is formed by grinding an outer round surface of the cylindrical body to reduce the diameter of the body. Since the cylindrical intermediate material has the hardness profile changing coaxially as described above, the neck portion 3 formed by grinding the outer round surface has a hardness relatively less than the cutting section 1 and the shank 2 which remain the outer round surface thereof. Therefore, when a prescribed weight is exerted on the neck portion 3, the neck portion 3 tends to be broken down faster than the cutting section 1, thereby forming a safe Peeso reamer capable of preventing a part of the cutting section 1 from being chipped.

When the Peeso reamer A thus constituted is attached to a hand piece to conduct a treatment, the neck portion 3 rotates while the axis thereof is flexibly curving based on an effect from the drilling resistance and on the positional relation to the hand piece, because the entire material has the uniform hardness and because the neck portion 3 has the smaller diameter than other portions. The blades 1a drill the dentin by this rotation to conduct the treatment. Repetitive bending motions and repetitive use of the Peeso reamer A may increase the hardness and accumulate bending fatigue at the neck portion 3. Therefore, the Peeso reamer can be chipped only at the neck portion 3.

Referring to FIG. 3, a Gates drill B according to a second embodiment of the invention is described. The Gates drill B has a cutting section 1 in a droplet shape on a distal end of a drill body and a shank 12 having a predetermined length located on the other end of the drill body. A neck portion 13 of a smaller diameter is formed between the cutting section 11 and the shank 12.

This Gates drill B has a cutting section 11 only at the distal end; the cutting section 11 has a plurality of spiral blades 11a arranged at a predetermined twisted angle and a contour in a spherical shape. In the Gates drill of this embodiment, the austenitic stainless steel is cold-drawn and machined to form the cutting section 11 and the neck portion 13 on respective sides of the drill body. An end of the shank 12 is cut to form an orientation portion 12a to be coupled to the hand piece.

Referring to FIG. 4, a drill for implantation according to a third preferred embodiment of the invention is described. The drill C for implantation is a rotary drilling instrument used for drilling a jaw or tooth to form a hole into which a post is buried and secured during a surgical implantation treatment in which the post is implanted into the jaw or tooth for supporting an artificial tooth. The drill for implantation, as well as the Peeso reamer and the Gates drill, is formed with a cutting section 21 at an distal end of a drill body and with a shank 22 located on the other end of the drill body with an orientation portion 22a.

A neck portion 23 of a smaller diameter is formed between the cutting section 21 and the shank 22. A sleeve 24 is formed at a portion of the shank 22 to serve as a stopper for controlling a drilled depth when a jaw is drilled in use of this drill C for implantation. The drill C for implantation is formed with spiral blades 21a across the entire cutting section 21 and a couple of wide flutes in a slightly spiral shape. In the drill C for implantation of the embodiment, the austenitic stainless steel is cold-drawn to form a stick, and the surface of the stick is then machined to form the cutting section 21 and the neck portion 23 on respective sides of the drill body.

As described above, in the Peeso reamer, the Gates drill, and the drill for implantation, no deviation of hardness occurs because the surface hardness is set at a predetermined value (Hv 500 or more) while the austenitic stainless steel having the organization elongated to be fibriform is used for the respective bodies, and those instruments have substantially the same drilling ability as a rotary drilling instrument made of a hardened steel or martensitic stainless steel. In particular, though the Peeso reamer and the Gates drill may be used in bent conditions, the neck portion of those instruments is flexibly bent and capable of drilling the dentin, because the fibriform organization elongated in the longitudinal direction is strong against bending. The neck portion has a lower hardness than the cutting section and the shank because the harder surface at the neck portion is ground away, so that only the neck portion can be broken down, thereby improving safety during treatments. Those instrument can also maintain a clean condition free from rust even subject to repetitive use and sterilization by the virtue of the austenitic stainless steel.

It is to be noted that in the embodiments above, the shown shapes of the Peeso reamer, the Gates drill, and the drill for implantation are merely examples, and it is as a matter of course that those instrument may be modified into various shapes according to shapes of teeth to be treated and therapies. In particular, although any of the embodiments above is exemplifying the instrument with spiral blades, it is as a matter of course that the instrument can have straight blades extending in parallel with the axis of the instrument.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not to be limited by the specification, but be defined by the claims set forth below.

What is claimed is:

1. A method for manufacturing a rotary drilling instrument, comprising the steps of:

cold-drawing an austenitic stainless steel to form a shaft-shape material having fibriform organization elongated in a longitudinal direction of the shaft-shape material and having a hardness profile changing harder from a center to a round surface coaxially;

forming a cutting portion at one end of the shaft-shape material and shank portion at the other end of the shaft-shape material;

forming a neck portion between the cutting portion and the shank portion by grinding to remove hard outer round surface of the neck portion.

2. The method of manufacturing a rotary drilling instrument of claim 1, further comprising forming said neck portion with a smaller diameter than said shank portion by grinding a coarse bonding outer round surface of said shaft-shaped material.

3. The method of manufacturing a rotary drilling instrument of claim 2, further comprising forming said cutting portion formed from a distal end of said shaft-shaped material in a mid point of said shaft-shaped material extending a predetermined length so as to form a Peeso reamer.

4. The method of manufacturing a rotary drilling instrument of claim 1, further comprising forming said cutting portion only at a distal end of said shaft-shaped material so as to form a Gates drill.

5. The method of manufacturing a rotary drilling instrument of claim 1, further comprising forming said cutting portion having blades suitable for drilling jaw teeth to form a hole for implantation.

* * * * *